(12) United States Patent
Mizukami

(10) Patent No.: US 11,111,595 B2
(45) Date of Patent: Sep. 7, 2021

(54) APPARATUS FOR ELECTROLYTIC ETCHING AND DISSOLUTION AND METHOD FOR EXTRACTING METAL COMPOUND PARTICLES

(71) Applicant: NIPPON STEEL & SUMITOMO METAL CORPORATION, Tokyo (JP)

(72) Inventor: Kazumi Mizukami, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 60 days.

(21) Appl. No.: 15/999,791

(22) PCT Filed: Feb. 17, 2017

(86) PCT No.: PCT/JP2017/005995
§ 371 (c)(1),
(2) Date: Aug. 20, 2018

(87) PCT Pub. No.: WO2017/142084
PCT Pub. Date: Aug. 24, 2017

(65) Prior Publication Data
US 2020/0141843 A1 May 7, 2020

(30) Foreign Application Priority Data
Feb. 18, 2016 (JP) .............................. JP2016-028895

(51) Int. Cl.
*C25F 3/02* (2006.01)
*C25F 3/06* (2006.01)
(Continued)

(52) U.S. Cl.
CPC ................. *C25F 3/02* (2013.01); *C25F 3/06* (2013.01); *C25F 7/00* (2013.01); *G01N 1/32* (2013.01);
(Continued)

(58) Field of Classification Search
CPC ....................................................... C25F 3/06
See application file for complete search history.

(56) References Cited

U.S. PATENT DOCUMENTS

2006/0006074 A1  1/2006  Liu et al.
2009/0139875 A1  6/2009  Kim et al.
(Continued)

FOREIGN PATENT DOCUMENTS

JP   59-141035 A    8/1984
JP   62-238379 A   10/1987
(Continued)

OTHER PUBLICATIONS

Taiwanese Office Action and Search Report, dated Mar. 9, 2018, for corresponding Taiwanese Application No. 106105333.
(Continued)

*Primary Examiner* — Brian W Cohen
(74) *Attorney, Agent, or Firm* — Birch, Stewart, Kolasch & Birch, LLP

(57) ABSTRACT

The object of the present invention is such that a surface exchange of metal fine particles by Cu ions, or the like is inhibited in order to prevent formation of Artificial CuS or the like, in extraction and analysis of the metal fine particles (inclusions and precipitates) in a metal material by electrolytic corrosion in a solvent-based electrolytic solution, without significantly changing conventional extraction and analysis methods, and such that the metal deposited on the cathode is actively attached to the cathode so that the deposited metal does not become a contamination source.
An apparatus for electrolytic etching and dissolution and an extraction method for separation and extraction of metal compound particles in a metal material,
  wherein at least a part of the cathode comprises a material consisting of a metal M' whose Δ defined by the
(Continued)

following formula is 10 or more, and the apparatus comprises an electrolytic cell for containing an electrolytic solution comprising a chemical agent that forms a complex containing the metal M' and a non-aqueous solvent, $$\Delta = pKsp[M'x'Ay'] - pKsp[MxAy] =$$
$$(-\log_{10}Ksp[M'x'Ay']) - (-\log_{10}Ksp[MxAy]).$$

20 Claims, 5 Drawing Sheets

(51) Int. Cl.
 C25F 7/00 (2006.01)
 G01N 1/32 (2006.01)
 G01N 1/40 (2006.01)
 G01N 33/2028 (2019.01)
(52) U.S. Cl.
 CPC ........... *G01N 1/40* (2013.01); *G01N 33/2028* (2019.01); *G01N 2001/4038* (2013.01)

(56) References Cited

U.S. PATENT DOCUMENTS

| 2010/0291692 | A1 | 11/2010 | Kinoshiro et al. |
| 2011/0019187 | A1* | 1/2011 | Mizukami .......... G01N 30/0005 356/335 |
| 2016/0185371 | A1 | 6/2016 | Churchvara et al. |

FOREIGN PATENT DOCUMENTS

| JP | 4-143290 A | 5/1992 |
| JP | 7-260772 A | 10/1995 |
| JP | 2000-137015 A | 5/2000 |
| JP | 2002-303620 A | 10/2002 |
| JP | 2002-363713 A | 12/2002 |
| JP | 2004-317203 A | 11/2004 |
| JP | 2006-274293 A | 10/2006 |
| JP | 2007-127454 A | 5/2007 |
| JP | 2009-131949 A | 6/2009 |
| JP | 2013-107381 A | 6/2013 |
| JP | 2015-52589 A | 3/2015 |
| JP | 2018-500237 A | 1/2018 |
| KR | 10-1163299 B1 | 7/2012 |
| SU | 1257446 A1 | 9/1986 |
| SU | 1755103 A1 | 8/1992 |

OTHER PUBLICATIONS

Tan et al., "Formation of Copper Sulfide Artifacts During Electrolytic Dissolution of Steel," Metallurgical and Materials Transactions, vol. 44B. No. 3, Jun. 2013 (Published online Mar. 16, 2013), pp. 483-486.

Russian Search Report and English translation of the Notice of Allowance for corresponding Russian Application No. 2018132868/02, dated Jun. 10, 2019 with English translation of the Search Report.

Extended European Search Report dated Sep. 9, 2019, for corresponding European Application No. 17753338.7.

Deguchi, "Electrolytic Etching Machining by Ethylene Glycol Solutions", Surface Technology, vol. 61, No. 4, 2010, pp. 305-308.

Information Statement dated Jul. 16, 2019, for corresponding Japanese Patent Application No. 2018-500235, with English translation.

Japanese Notice of Reasons for Refusal dated Jul. 9, 2019, for corresponding Japanese Application No. 2018-500237, with English translation.

Kobayashi et al., "Breakdown Characteristics of Oxygen-Free Copper Electrodes in Ultrahigh Vacuum", Electron Theory A, vol. 114, No. 2, 1996, pp. 91-99.

Steel Handbook, Cover, Table of Contents and Back page, Oct. 30, 1991, pp. 332-333, 4 pages total.

* cited by examiner

Result of chemical analysis for Mn and Cu

FIG. 4

Table 1: The solubility products of the sulfides in an aqueous solution at 25°C and the pKsp difference Δ of the sulfides.

| No | Compound | Formula | $K_{sp}$ (at 25°C) | $pK_{sp}$ | HgS | Ag$_2$S | CuS | PbS | CdS | NiS | ZnS | CoS | Tl$_2$S | FeS |
|---|---|---|---|---|---|---|---|---|---|---|---|---|---|---|
| 1 | Mercury(II) sulfide (red) | HgS | 2 × 10^−54 | 53.7 | | | | | | | | | | |
| 2 | Silver(I) sulfide | Ag$_2$S | 8 × 10^−51 | 50.1 | 3.6 | 0.0 | | | | | | | | |
| 3 | Copper(II) sulfide | CuS | 8 × 10^−37 | 36.1 | 17.6 | 14.0 | 0.0 | | | | | | | |
| 4 | Lead(II) sulfide | PbS | 3 × 10^−28 | 27.5 | 26.2 | 22.6 | 8.6 | 0.0 | | | | | | |
| 5 | Cadmium sulfide | CdS | 1 × 10^−27 | 27.0 | 26.7 | 23.1 | 9.1 | 0.5 | 0.0 | | | | | |
| 6 | Nickel(II) sulfide (beta) | NiS | 1.3 × 10^−25 | 24.9 | 28.8 | 25.2 | 11.2 | 2.6 | 2.1 | 0.0 | | | | |
| 7 | Zinc sulfide (alpha) | ZnS | 2 × 10^−25 | 24.7 | 29.0 | 25.4 | 11.4 | 2.8 | 2.3 | 0.2 | 0.0 | | | |
| 8 | Cobalt(II) sulfide (beta) | CoS | 3 × 10^−26 | 24.5 | 29.2 | 25.6 | 11.6 | 3.0 | 2.5 | 0.4 | 0.2 | 0.0 | | |
| 9 | Thallium(I) sulfide | Tl$_2$S | 6 × 10^−22 | 21.2 | 32.5 | 28.9 | 14.9 | 6.3 | 5.8 | 3.7 | 3.5 | 3.3 | 0.0 | |
| 10 | Iron(II) sulfide | FeS | 8 × 10^−19 | 18.1 | 35.6 | 32.0 | 18.0 | 9.4 | 8.9 | 6.8 | 6.6 | 6.4 | 3.1 | 0.0 |
| 11 | Manganese(II) sulfide (green) | MnS | 3 × 10^−14 | 13.5 | 40.2 | 36.6 | 22.6 | 14.0 | 13.5 | 11.4 | 11.2 | 11.0 | 7.7 | 4.6 |

■ Combination in which the pKsp difference Δ is 22 or more (CuS vs MnS) (Expecting degree of exchange reaction √√)

▨ The pKsp difference Δ is 10 or more and less than 22, and ion exchange reaction is expected (√√ to √)

☐ The pKsp difference Δ is less than 10, and expecting degree of ion exchange reaction is low (√ to ×)

FIG. 5

Table 4: the pKsp difference Δ of the selenides in an aqueous solution at 25°C

| No | Compound | Formula | $K_{sp}$ (at 25°C) | $pK_{sp}$ | HgSe | Ag$_2$Se | CuSe | PbSe | CdSe | Tl$_2$Se | NiSe | CoSe | ZnSe | FeSe |
|----|----------|---------|-----|-----|------|------|------|------|------|------|------|------|------|------|
| 1 | Mercury(II) selenide | HgSe | | 64.5 | | | | | | | | | | |
| 2 | Silver(I) selenide | Ag$_2$Se | | 63.7 | 0.8 | | | | | | | | | |
| 3 | Copper(II) selenide | CuSe | | 48.1 | 16.4 | 15.6 | 0 | | | | | | | |
| 4 | Lead(II) selenide | PbSe | | 42.1 | 22.4 | 21.6 | 6 | 0 | | | | | | |
| 5 | Cadmium selenide | CdSe | | 35.2 | 29.3 | 28.5 | 12.9 | 6.9 | 0 | | | | | |
| 6 | Thallium(I) selenide | Tl$_2$Se | | 33.1 | 31.4 | 30.6 | 15 | 9 | 2.1 | 0 | | | | |
| 7 | Nickel(II) selenide | NiSe | | 32.7 | 31.8 | 31 | 15.4 | 9.4 | 2.5 | 0.4 | 0 | | | |
| 8 | Cobalt(II) selenide | CoSe | | 31.2 | 33.3 | 32.5 | 16.9 | 10.9 | 4 | 1.9 | 1.5 | 0 | | |
| 9 | Zinc selenide | ZnSe | | 29.4 | 35.1 | 34.3 | 18.7 | 12.7 | 5.8 | 3.7 | 3.3 | 1.8 | 0 | |
| 10 | Iron(II) selenide | FeSe | | 22 | 42.5 | 41.7 | 26.1 | 20.1 | 13.2 | 11.1 | 10.7 | 9.2 | 7.4 | 0 |
| 11 | Manganese(II) selenide | MnSe | | 11.5 | 53 | 52.2 | 36.6 | 30.6 | 23.7 | 21.6 | 21.2 | 19.7 | 17.9 | 10.5 |

 Combination in which the pKsp difference Δ is 22 or more (CdSe vs MnSe) (Expecting degree of exchange reaction √√)

 The pKsp difference Δ is 10 or more and less than 22, and ion exchange reaction is expected (√√ to √)

 The pKsp difference Δ is less than 10, and expecting degree of ion exchange reaction is low (√ to ×)

APPARATUS FOR ELECTROLYTIC ETCHING AND DISSOLUTION AND METHOD FOR EXTRACTING METAL COMPOUND PARTICLES

FIELD

The present invention relates to an apparatus for electrolytic etching and dissolution for separation and extraction of metal compound particles in a metal material, wherein at least part of a cathode comprises a material made of a certain metal.

BACKGROUND

It is widely practiced to control strengths and characteristics of metal materials, in particular, steel materials to the required level by controlling types of inclusions and precipitates present in the material matrix, their shapes such as aspect ratios and their dimensions, as a result of trace amounts of added elements and various heat treatments.

Therefore, observation of inclusions and/or precipitates, and measurement of components and amounts thereof have important meanings in quality control of steel materials and analysis of manufacturing processes.

In order to observe inclusions and precipitates by SEM or the like, it is necessary to expose the inclusions and precipitates buried in the matrix to the observation surface. Conventionally, the inclusions and precipitates are exposed to the surface of sample to make it observable by electrolytic dissolution of the sample in various electrolyte solutions.

In recent years, due to the progress of the manufacturing technology of steel materials, the types of inclusions and precipitates are diversified, and they are finely dispersed. For their observation, it is required for an electrolyte solution to selectively dissolve only the matrix (Fe), but not to dissolve inclusions and precipitates, even if they are fine grains, so that the inclusions and precipitates would surely retain on the observation surface.

In addition, when identifying and quantitatively analyzing these inclusions and precipitates, the matrix of the steel sample is dissolved in the electrolyte solution, and phases are collected as an electrolytic residue to carry out their identification and quantitative analysis.

In the case of this quantitative analysis, it is necessary that only the matrix portion of the steel material is efficiently electrolyzed, the Fe component is reliably dissolved to be retained in the electrolytic solution, and the other portion corresponding to inclusions and precipitates is surely recovered as an electrolytic residue.

Patent Document 1 describes an electrolytic solution composition for a steel sample, and a method for analyzing inclusions and precipitates using the same.

On the contrary that many of the conventional electrolytic solutions were acidic, this electrolytic solution composition comprises an added alkaline triethanolamine. As a result, particles of the inclusions and precipitates are rarely dissolved and tend to remain on the surface of the steel material sample, even if the inclusions and precipitates are fine. Accordingly, after taking out the steel sample from the electrolytic solution and drying it, it is possible to observe and analyze the inclusions and precipitates as they are by SEM or the like.

In addition, Patent Document 2 discloses inventions relating to a nonaqueous solvent based electrolytic solution for extracting inclusions and precipitates in a steel sample and a method for electrolytically extracting a steel sample using the same.

This electrolytic solution contains maleic anhydride, tetramethylammonium chloride and methanol in a predetermined ratio, and is an electrolyte solution excellent in the ability to electrolyze a large amount of steel sample at a time. It is characterized in that maleic anhydride contained in the solution forms an iron complex and prevents formation of complex precipitate such as Fe hydroxide.

In order to observe inclusions and precipitates in a steel sample in situ by SEM or the like, it is necessary to electrolyze the sample so that the matrix constituting Fe component is retained in the electrolytic solution with the Fe ion chelating agent and the inclusions and precipitates remain on the sample surface.

On the other hand, in the case of quantitative analysis of inclusions or precipitates, the Fe component of the matrix is retained in the electrolytic solution by a chelating agent, and by using an electrolytic solution which does not dissolve the inclusions and precipitates separated from the sample by electrolytic dissolution, the inclusions and precipitates are recovered as an electrolytic residue to identify and quantitatively analyze the residue.

Therefore, in the case of aiming for the collection of a residue for identification and quantitative analysis of inclusions and precipitates, the main focus is on maintaining Fe component in the dissolved state as chelate complex in the electrolytic solution. No particular consideration was given to contamination of the inclusions and the precipitates in the electrolytic operation.

PRIOR ART DOCUMENT

[Patent Document]
[PATENT DOCUMENT 1] Japanese Unexamined Patent Publication (Kokai) No. 2002-303620
[PATENT DOCUMENT 2] Japanese Unexamined Patent Publication (Kokai) No. 2000-137015

SUMMARY

Problems to be Solved by the Invention

In analyzing metal compounds in steel materials, for example, by electrolytic corrosion in a conventional non-aqueous solvent-based electrolytic solution, an unknown phenomenon that higher content of CuS is observed than that measured by means other than the electrolytic operation has sometimes been observed for fine particles of inclusions and precipitates, particularly of various metal compounds, especially on MnS surface layer. Accordingly, it is believed that MnS particles are detected as if it were CuS (Artificial CuS).

The inventors of the present invention have studied in detail the cause thereof. As a result, it was discovered that, when a metal ion having a small solubility product Ksp ($Cu^{2+}$) is produced in the electrolytic solution by an electrolytic operation, a metal ion having a large Ksp solubility product ($Mn^{2+}$) is exchanged with the metal ion having a small solubility product Ksp ($Cu^{2+}$) on the surface of the metal sulfide (MnS). It was also found that the exchange of metal ions on the sulfide surface would easily proceed at a normal temperature and a normal pressure even in an aqueous solution or a nonaqueous solvent.

As a result, inclusions and precipitates which originally existed as MnS in the steel sample were observed as CuS, when the surface of the sample was observed. Further, in the case of fine particles, where CuS derived from Cu ions in the electrolytic solution is exchanged with MnS to the depth of several tens of nm (1 to 100 nm) from the surface of MnS, a substantial portion of the volume of the fine particles will be occupied by CuS. Therefore, it became impossible to accurately quantify MnS, even if mass spectrometry is performed to a sample from the residue.

In the above description, although the case of attack on the MnS surface by Cu (exchange phenomenon of Mn atom by Cu atom on the MnS surface) was explained, it can be presumed that similar phenomena may occur for metals other than Cu. That is, it can be presumed that exchange of metal ions on the surface of the metal compound will easily proceed when there is a certain difference between a larger solubility product Ksp and a smaller solubility product Ksp (in order of 10 digits ($10^{10}$) or more). In the specification, this phenomenon is referred to as "Artifact." More specifically, when the difference in pKsp between two compounds having different solubility products Ksp (hereinafter sometimes referred to as A) is about 10 or more, it is estimated that an exchange between the compound having a larger pKsp (smaller solubility product Ksp) and the compound having a smaller pKsp (larger solubility product) will easily proceed.

The above condition can be expressed by the following equation.

$$\Delta = pKsp[\text{compound(smaller }Ksp)] - pKsp[\text{compound(larger }Ksp)] =$$
$$(-\log_{10} Ksp[\text{compound(smaller }Ksp)] -$$
$$(-\log_{10} Ksp[\text{compound(larger }Ksp)]) \geq 10,$$

where, the solubility product Ksp of a certain compound is expressed as Ksp [compound], and pKsp [compound]=−$\log_{10}$ Ksp [compound].

In fact, it was confirmed that, when a simulation experiment in which Ag exerts on MnS was carried out by the inventors, Ag attacked MnS to ionize Mn and expel it into the electrolytic solution and Ag, itself remained as $Ag_2S$ on the surface of MnS. Comparing the solubility product (or pKsp) of $Ag_2S$ with that of MnS, $Ag_2S$ has a smaller solubility product Ksp (larger pKsp) and MnS has a larger solubility product Ksp (smaller pKsp). The difference in the solubility products Ksp between $Ag_2S$ and MnS is 37 digits, and the pKsp difference $\Delta$ is 36.6. It is expressed by the following equation.

$$\Delta = pKsp[Ag_2S] - pKsp[MnS] = 50.1 - 13.5 = 36.6 \geq 10$$

Further, the inventors of the present invention have made the following discovery. In the electrolytic operation, some of ions may be deposited onto a cathode. However, if the affinity of the deposited metal and the constituent material of the cathode is not high, then the deposited metal easily peels off and again precipitates as metal, or becomes a source of metal ions, and as a result, it can become a contamination source of the inclusions, precipitates and electrolytic residue.

The problems to be solved by the present invention are as follows.

In the extraction and analysis of metal fine particles (inclusions and precipitates) in metal materials by electrolytic corrosion method or the like in a solvent-based electrolytic solution, formation of Artificial CuS and the like is prevented by inhibiting a surface exchange of the metal fine particles with Cu ions and the like.

Formation of Artificial CuS and the like is prevented particularly on metal sulfides (MnS, FeS etc.).

Making the deposited metals such as Cu on the cathode actively attach to the cathode so that the metal does not easily peel off and precipitate to be a contamination source of the inclusions, precipitates and electrolytic residue.

Means for Solving the Problem

The inventors of the present invention have conducted intensive studies on a strategy for solving the above-mentioned problems.

As a result, from the observation that an exchange phenomenon does not occur unless a metal that forms Artifact metal sulfide (referred to as "attack metal") is present in the solvent-based electrolytic solution, it was conceived that capturing such an attack metal would be effective. That is, it was conceived that, if a material made of a metal element to be captured is placed on at least a part of the cathode of the electrolytic apparatus to facilitate electrodeposition of the metal on the cathode and the deposited attack metal is held on the cathode, then a free attack metal in the electrolytic solution will be reduced, and no Artifact metal sulfide will be produced.

When matrix (Fe) ions dissolve out from a steel sample or the like by electrolytic dissolution, Fe ions are retained in the electrolyte solution by a chelating agent. Meanwhile, metal ions other than the matrix (Fe), such as Cu ions, may dissolve out by electrolytic dissolution, and such ions (for example, Cu ions) may migrate to and deposit on the cathode. However, since there is no trapping site after deposition, the deposit can easily peel off from the cathode, precipitate as metal Cu in the electrolytic solution, and serve as a supply source of metal ions (Cu ions etc.). That is, it can be a contamination source of inclusions, precipitates and electrolytic residue. By positively placing a trapping site (deposition site) for attaching such a metal ion (Cu ion or the like) as a deposition metal, the metal ions (Cu ions or the like) will not peel off and precipitate after electrolytic deposition at the cathode. As a result, it was found that the supply source of metal ions (Cu ions or the like) into the electrolytic solution can be reduced. Accordingly, for example, by preventing Cu ions from attacking MnS on the surface of the steel sample for surface observation, or similarly by preventing a metal Cu or CuS, from incorporating into a residue for quantitative analysis made from inclusions and precipitates, it is possible to observe the inclusions and precipitates in the steel sample for surface observation as their original form. In addition, since the electrolytic residue for analysis does not contain metal Cu and CuS or the like derived from Cu ions dissolved from the matrix or the like of the sample, it is possible to precisely identify and quantify only the elements derived from the inclusions and precipitates contained in the original steel sample.

The present invention has been made on the basis of the above findings, and its summary is as follows.

(1) An apparatus for electrolytic etching and dissolution for separation and extraction of metal compound particles in a metal material, the apparatus comprising an anode and a cathode, and electrolytically etching the metal material by electrifying between the anode and the cathode, wherein at least a part of the cathode comprises a material comprising a metal M' whose Δ defined by the following formula is 10 or more, and the apparatus comprises an electrolytic cell for containing an electrolytic solution comprising a chemical agent that forms a complex containing said metal M' and a nonaqueous solvent, $$\Delta = pKsp[M'x'Ay'] - pKsp[MxAy] =$$
$$(-\log_{10}Ksp[M'x'Ay']) - (-\log_{10}Ksp[MxAy])$$

wherein a solubility product of metal compound M'x'Ay' is defined as Ksp[M'x'Ay'], and a solubility product of metal compound to be extracted MxAy, which is contained in the metal material, is defined as Ksp[MxAy], and wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

(2) The apparatus for electrolytic etching and dissolution according to item (1) above, wherein the metal compound to be extracted MxAy is one or two of MnS or FeS.

(3) The apparatus for electrolytic etching and dissolution according to item (1) or (2) above, wherein the metal M' of the metal compound M'x'Ay' is at least one of Hg, Ag, Cu, Pb, Cd, Co, Zn and Ni.

(4) The apparatus for electrolytic etching and dissolution according to any one of items (1) to (3) above, wherein said material comprised in the cathode is provided to cover a surface of the cathode.

(5) The apparatus for electrolytic etching and dissolution according to any one of items (1) to (3) above, wherein the cathode is made of said metal M'.

(6) The apparatus for electrolytic etching and dissolution according to any one of items (1) to (5) above, wherein said material comprised in the cathode consists of 99.9% by mass or more of Cu and inevitable impurities.

(7) The apparatus for electrolytic etching and dissolution according to any one of items (1) to (6), wherein said nonaqueous solvent comprises at least one of methanol or ethanol.

(8) The apparatus for electrolytic etching and dissolution according to any one of items (1) to (7), wherein the chemical agent that forms a complex containing the metal M' comprises at least one of polyethylene amines, ethylenediamine tetraacetic acid and cyclohexanediamine tetraacetic acid.

(9) The apparatus for electrolytic etching and dissolution according to item (8), wherein the chemical agent comprises triethylenetetramine.

(10) The apparatus for electrolytic etching and dissolution according to any one of items (1) to (9), wherein it comprises a stirring means for the electrolytic solution.

(11) The apparatus for electrolytic etching and dissolution according to item (10), wherein it further comprises a gas bubble generator for irradiating a bubble to the anode surface.

(12) A method for extracting metal compound particles in a metal material, by providing an anode and a cathode, and electrolytically etching the metal material by electrifying between the anode and the cathode, wherein at least a part of the cathode surface comprises a material comprising a metal M' whose Δ defined by the following formula is 10 or more, and the method uses an electrolytic solution comprising a chemical agent that forms a complex containing said metal M' and a nonaqueous solvent, $$\Delta = pKsp[M'x'Ay'] - pKsp[MxAy] =$$
$$(-\log_{10}Ksp[M'x'Ay']) - (-\log_{10}Ksp[MxAy])$$

wherein a solubility product of metal compound M'x'Ay' is defined as Ksp[M'x'Ay'], and a solubility product of metal compound to be extracted MxAy, which is contained in the metal material, is defined as Ksp[MxAy], and wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

(13) The method for extracting metal compound particles according to item (12), wherein the electrolytic etching is performed with stirring the electrolytic solution during the electrolytic etching process.

(14) The method for extracting metal compound particles according to item 13, wherein the electrolytic solution is stirred with a magnetic stirrer.

(15) The method for extracting metal compound particles according to item (13), wherein a gas bubble is bubbled in the electrolytic solution.

Effect of the Invention

According to the present invention, by analyzing the surface of the extracted metal fine particles, MnS or FeS fine particles are no longer misidentified as CuS, and the true appearance (size, component) of the metal sulfide can be known. In addition, the content of metal sulfide in the steel material can be accurately measured.

According to the present invention, it becomes possible that inclusions or precipitates and the like exposed on the surface of the steel sheet by electrolytic operation are observed as the same components and form originally present in the steel sample. Further, in a quantitative analysis of inclusions and precipitate components from the analysis of the electrolytic residue, it is possible to accurately perform a quantitative analysis without being influenced by Cu or the like incorporated from the electrolytic solution. Therefore, observation of the structure of the steel sample, and identification and quantitative analysis of the inclusions and precipitates can be greatly improved.

BRIEF DESCRIPTION OF DRAWINGS

FIG. 4 is Table 1, which shows the solubility products Ksp of the sulfides in an aqueous solution at 25° C., and the pKsp($=-\log_{10}$ Ksp) difference Δ between the sulfides.

FIG. 5 is Table 4, whch shows the pKsp(=−log$_{10}$ Ksp) difference Δ among selenides in an aqueous solution at 25° C.

DESCRIPTION OF EMBODIMENTS

According to the present invention, there is provided an apparatus for electrolytic etching and dissolution for separation and extraction of metal compound particles in a metal material, the apparatus comprising an anode and a cathode, and electrolytically etching the metal material by electrifying between the anode and the cathode, wherein at least a part of the cathode comprises a material comprising a metal M' whose Δ defined by the following formula is 10 or more, and the apparatus comprises an electrolytic cell for containing an electrolytic solution comprising a chemical agent that forms a complex containing said metal M' and a nonaqueous solvent, $$\Delta = pKsp[M'x'Ay'] - pKsp[MxAy] =$$
$$(-\log_{10}Ksp[M'x'Ay']) - (-\log_{10}Ksp[MxAy])$$

wherein a solubility product of metal compound M'x'Ay' is defined as Ksp[M'x'Ay'], and a solubility product of metal compound to be extracted MxAy, which is contained in the metal material, is defined as Ksp[MxAy], and wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

In the apparatus for electrolytic etching and dissolution of the present invention, metal compound particles in the metal material are extracted. That is, by etching the metal material in the electrolytic solution, a matrix (Fe or the like) is selectively dissolved to expose metal compound particles such as inclusions and precipitates contained in the metal material onto the sample surface. This makes it possible to observe the metal compound particles.

Figure 1:
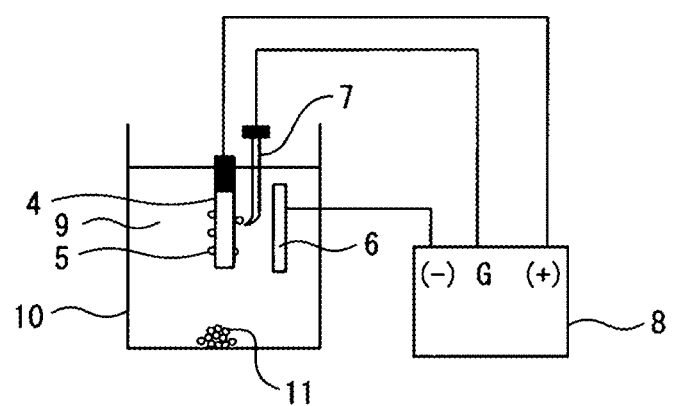
FIG. 1 shows an example of a sketch of an apparatus for electrolytic etching and dissolution according to the present invention.

As a method for extracting fine particles in a metal sample, for example, an acid decomposition method of dissolving an iron matrix of a steel sample in an acid solution, a halogen dissolution method wherein an iron matrix of a steel sample is dissolved in a iodine/methanol mixed solution or a bromine/methanol mixed solution, a nonaqueous solvent constant current electrolytic dissolution method and a nonaqueous solvent-based potentiostatic electrolytic method (SPEED: Selective Potentiostatic Etching by Electrolytic Dissolution Method), or the like can be used. Among them, SPEED method using a nonaqueous solvent is preferable because a change in composition and size rarely occurs when fine particles are dispersed in a solvent, and thus even unstable fine particles can be stably extracted. With respect to the present embodiment, an explanation will be given by taking an evaluation method of fine particles in a steel material by a general electrolytic extracting method: Selective Potentiostatic Etching by Electrolytic Dissolution Method (SPEED method) with reference to FIG. 1. However, the extraction method in the present invention is not limited to SPEED method.

Initially, the metal sample 4 is processed to a size of, for example, 20 mm×40 mm×2 mm, an oxide film such as a scale on the surface layer is removed by chemical polishing or mechanical polishing or the like to reveal a metal layer. Conversely, when analyzing microparticles contained in the oxide film layer, the surface layer should be left as it is.

Next, the following explanation is based an example where this metal sample is electrolyzed by using SPEED method. Specifically, the electrolytic solution 9 is filled in the electrolytic cell 10, the metal sample 4 is immersed in the electrolytic solution 9, and the reference electrode 7 is brought into contact with the metal sample 4. The platinum electrode 6 and the metal sample 4 are connected to the electrolytic apparatus 8. By electrifying between the metal sample 4 and the platinum electrode 6, the platinum electrode 6 can serve as a cathode. Generally, when the above electrolytic method is used, the electrolytic potential of fine particles such as precipitates in the steel is higher than that of the metal portion being a matrix of the metal sample 4. Therefore, it is possible to selectively dissolve only the matrix by setting an electrolytic potential using the electrolytic apparatus 8 at which the matrix of the metal sample 4 is dissolved and fine particles such as precipitates are not dissolved. The inclusions or the precipitates 5 emerge on the surface of the sample where Fe in the surface matrix portion is electrolytically eluted, and become suitable for observation by SEM or the like. Further, electrolytic dissolution may be continued to separate the inclusions or precipitates from the surface of the sample to recover them as the electrolytic residue 11 by filtrating and separating them from the electrolytic solution, and then the residue 11 may be subjected to identification and quantitative analysis.

An electrolytic solution for the metal material according to the present invention, that is, an electrolytic solution to electrolyze the surface Fe matrix for observation of the inclusions and precipitates, to electrolyze the Fe matrix for quantitative analysis of the inclusions and precipitates, and to be used for electrolytic dissolution for recovering the residue preferably comprises, (1) a complex forming agent for Fe ions,
(2) an electrolyte for ensuring conductivity in the electrolytic solution, and
(3) a solvent for retaining the formed complex such as Fe complex in the solution.

As the complex forming agent for Fe ions, one or more of acetylacetone, maleic anhydride, maleic acid, triethanolamine, salicylic acid and methyl salicylate may be selected.

As the electrolyte, one or more of tetramethylammonium chloride (TMAC), sodium chloride (NaCl) and lithium chloride (LiCl) can be selected.

The solvent needs to be capable of retaining various complex forming agents and complexes of the complex forming agent and Fe in a dissolved state, and may be a nonaqueous solvent. In the aqueous electrolytic solution, various precipitates are decomposed even at relatively low electrolytic dissolution voltage (for example, −300 mV or less), whereas the nonaqueous solvent-based electrolytic solution has a wide stable electrolytic dissolution region and can be applied to almost all steel materials from superalloy, high alloy, stainless steel to carbon steel. When a nonaqueous solvent-based electrolytic solution is used, only dissolution of the matrix and (complexation) reaction of the dissolved Fe ion and the chelating agent occur, and the inclusions or precipitates 5 do not dissolve. Accordingly, "in situ" state three-dimensional observation and analysis on the base material can be performed. As the nonaqueous solvent, a compound which promotes electrolytic dissolution smoothly and dissolves a complexable organic compound and a carrier electrolyte is suitable. For example, a lower alcohol such as methanol, ethanol or isopropyl alcohol may be used. Methanol, ethanol or a mixture thereof may be selected.

In the conventional constant potential electrolytic dissolution method, for example, a 10% by mass of acetylacetone (hereinafter referred to as "AA")—1% by mass of tetramethylammonium chloride (hereinafter referred to as "TMAC")—methanol solution, or a 10% by mass of maleic anhydride—2% by mass of TMAC-methanol solution is used as an electrolytic solution. These electrolytic solutions are frequently used because an electrolytically eluted Fe preferably forms a complex and the produced Fe complex is dissolved in the electrolytic solution.

Metals other than the matrix (Fe) may be eluted in the electrolytic solution even though the amount thereof is relatively small as compared with the matrix (Fe). The inventors found that, when the eluted metal has a small solubility product Ksp (in other words, a high pKsp($=\log_{10}$ Ksp)) and the inclusions or precipitates 5, or the electrolytic residue 11 contain a metal compound of which metal has a large solubility product Ksp (pKsp is small), a metal ion having a large solubility product Ksp (pKsp is small) (for example, $Mn^{2+}$) is exchanged with a metal ion having a small solubility product Ksp (large pKsp) (for example, $Cu^{2+}$) on the surface of the metal compound. It is considered that, when the difference in solubility products Ksp is greater than or equal to 10 digits ($10^{10}$), or more specifically, when the pKsp difference Δ of two compounds having different solubility products Ksp is about 10 or more, the exchange of the metal ions will progress easily. It is considered that, when the difference in solubility product Ksp is greater than or equal to 20 digits ($10^{20}$), or more specifically, when the pKsp difference Δ is about 20 or more, the exchange of the metal ions will proceed more easily.

Table 1 in FIG. 4 shows the solubility products Ksp of the sulfides in an aqueous solution at 25° C., and the pKsp ($=-\log_{10}$ Ksp) difference Δ between the sulfides. In the table, the double line frame (or the dark gray frame) represents a combination of sulfides having the pKsp difference Δ of 22 or more, and it is expected that the exchange reaction easily proceeds or in units of seconds with these combinations. Expressed simply as a symbol, the expecting degree (prediction) of the exchange reaction is expressed as √√√. The thick line frame (or light gray frame) represents a combination of sulfides having the pKsp difference Δ of 10 or more and less than 22, and the exchange reaction is expected to proceed, but it may take from several minutes to several hours. Expressed simply by a symbol, the expecting degree (prediction) of the exchange reaction is expressed as √√ to √. The thin line frame (or the white frame) represents a combination of sulfides having the pKsp difference Δ of less than 10, and it is expected that the exchange reaction hardly progresses with these combinations. Expressed simply as a symbol, the expecting degree (prediction) of the exchange reaction is expressed as √ to x.

Incidentally, regarding a solubility product of the sulfides, some sulfides of the same element show different solubility products depending on the crystal form and the like. In Table 1, sulfides having crystal forms and the like in which the pKsp difference Δ is small are listed. This is because even when the pKsp difference Δ of the sulfides is large, the pKsp difference Δ of the sulfides in question becomes 10 or more, and it is considered that the exchange reaction will proceed.

Although the above solubility product Ksp is a value in an aqueous solution, it is presumed that the same tendency also occurs in a nonaqueous solvent such as similar polar solvent of methanol.

For example, when MnS is present on the steel sample surface or in the electrolytic solution residue, the sulfide of Cu ion eluted into the electrolytic solution has a pKsp difference against MnS of 22.6, so Cu ion attacks MnS. Then, Mn is ionized and expelled into the electrolytic solution, and Cu ion itself remains as CuS on the MnS surface. In other words, the inclusions and precipitates which originally existed as MnS in the Cu-containing steel sample are observed as CuS when their surface is observed. Even if mass spectrometry is performed from the residue, accurate quantification becomes impossible in the case of fine particles. It is so because CuS occupies a substantial portion of the volume of the fine particles, as CuS derived from Cu ions in the electrolytic solution exchange MnS to a thickness of about several tens of nanometers (1 to 100 nm) on the surface of MnS. The phenomenon in which such a metal near the surface is exchanged is sometimes referred to as Artifact in this specification.

Since the sulfide of Ag ion has a pKsp difference against MnS of 36.6, Ag ion attacks MnS. Then, Mn is ionized and expelled into the electrolytic solution, and Ag ion, itself remains as $Ag_2S$ on the MnS surface. This is confirmed in FIG. 3 obtained by the following procedure.

Prepare a steel sample which has been confirmed to contain MnS as inclusions, and preliminarily mirror polish the sample in order to remove surface impurities.

Prepare an electrolytic solution (4% MS) containing 4% by mass of methyl salicylate+1% by mass of salicylic acid+1% by mass of tetramethylammonium chloride (TMAC) in methanol solvent, which is conventionally known and capable of recovering sulfide inclusions as a residue.

Carry out electrolytic dissolution of the steel sample in the electrolytic solution.

After completion of electrolytic dissolution, add a droplet of Ag ion solution into the electrolytic solution and mix it.

Observation by scanning electron microscope (SEM) and measurement of surface element concentration by EDS are performed on the steel samples which are electrolyzed on their surfaces before and after adding a droplet of Ag ion solution.

Figure 3:
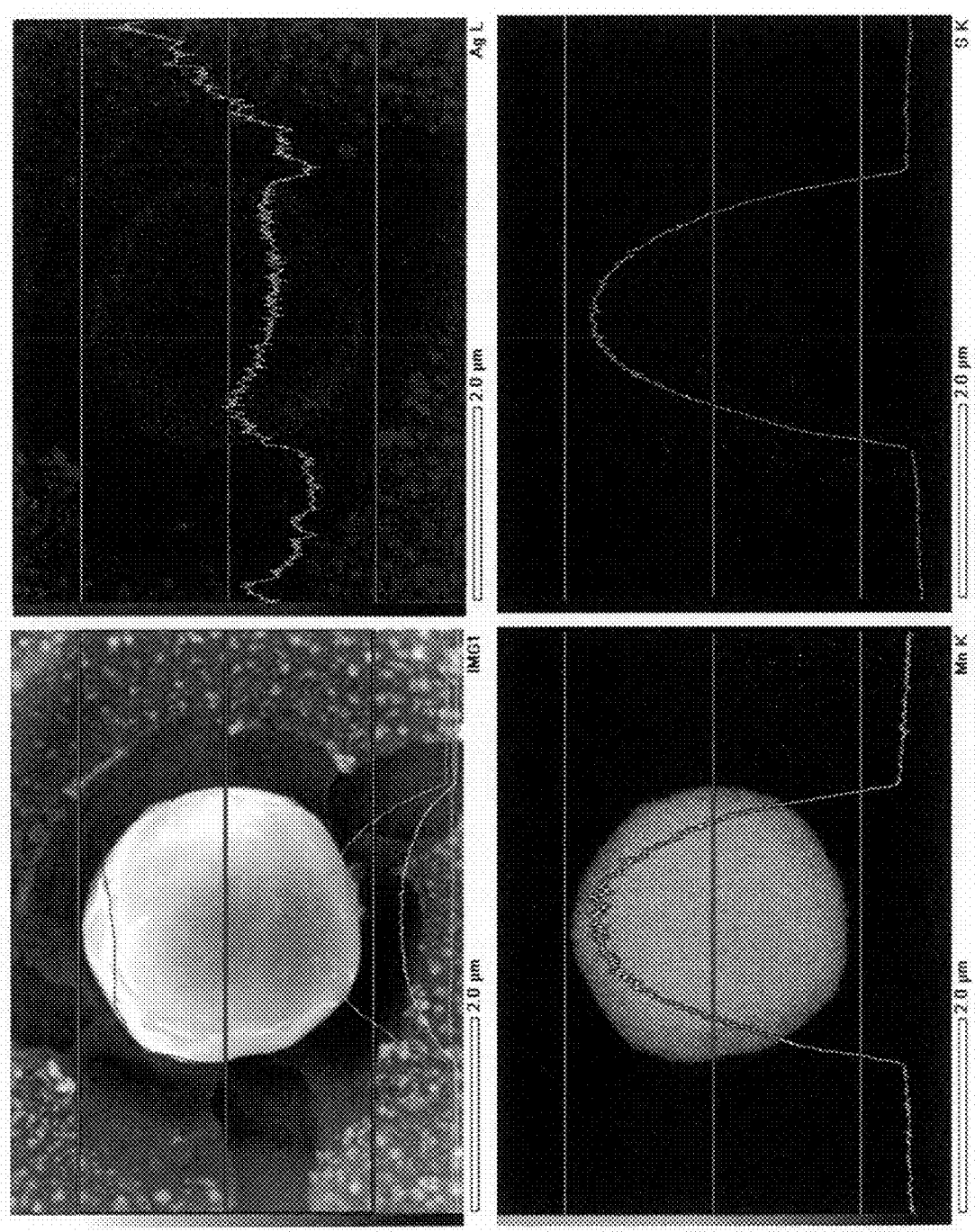
FIG. 3 is a SEM photograph and a graph showing element concentrations around inclusions of a mirror-polished steel sample.

FIG. 3 shows the results after adding a droplet of Ag ion. The upper left image shows the SEM observation image, the upper right image shows the SEM observation image and the chart of the Ag concentration measured by EDS in an overlapping manner, the lower left image shows the Mn concentration chart in an overlapping manner, and the lower right image shows the S concentration chart in an overlapping manner.

Incidentally, as a matter of course, Ag was not observed before adding a droplet of Ag ion.

From the chart of each element concentration in FIG. 3, it is confirmed that only the surface portion of the MnS particle is exchanged by $Ag_2S$. Although the height (concentration) of each element in the chart is relative, the following facts can be read. Specifically, in the inclusion particle portion, the values of Mn and S in the graphs are rising as a mountain shape, and the inclusion particles contain Mn and S. Specifically, it is confirmed that the particles contain MnS as a main component. It is confirmed that the concentration of Ag is increased at the end portion of the inclusion particles and Ag is concentrated on the surface of the inclusion particles. In addition, at the central portion of the inclusion particles, the concentration of Ag does not increase and the concentrations of Mn and S are high. Therefore, it is confirmed that only the surface of MnS is exchanged by Ag.

The inventors of the present invention newly found that, in the apparatus for electrolytic etching and dissolution for separation and extraction of metal compound particles in a metal material, the apparatus comprising an anode and a cathode, and electrolytically etching the metal material by electrifying between the anode and the cathode, by using a specific material being comprised in at least a part of the cathode, an amount of a free attack metal (M') in the electrolytic solution is reduced and Artifact can be prevented. The specific material comprises a metal (attack metal) M' of the metal compound M'x'Ay', wherein a solubility product of metal compound M'x'Ay' is defined as Ksp[M'x'Ay'], and a solubility product of metal compound to be extracted MxAy, which is contained in the metal material, is defined as Ksp[MxAy], and wherein $$\Delta = pKsp[M'x'Ay'] - pKsp[MxAy] =$$
$$(-\log_{10} Ksp[M'x'Ay']) - (-\log_{10} Ksp[MxAy]) \geq 10.$$

In addition, in was newly found that, by using an electrolytic solution comprising a chemical agent that forms a complex containing an attack metal M', an amount of a free attack metal in the electrolytic solution is reduced and Artifact can be prevented.

Incidentally, M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

When matrix (Fe) ions dissolve out from a steel sample or the like by electrolytic dissolution, the Fe ions are retained in the electrolytic solution by the chelating agent. Meanwhile, metal ions other than the matrix (Fe), for example, ions of the attack metal M' such as Cu may dissolve out by electrolytic dissolution, and such ions (for example, Cu ions) migrate to and deposit on the cathode. However, since there is no trapping site after deposition, the deposit can easily peel off from the cathode and be precipitate as metal Cu in the electrolytic solution, or it can serve as a supply source of the attack metal M'(Cu, etc.). That is, it can be a contamination source of the inclusions, precipitates and electrolytic residue.

In the apparatus for electrolytic etching and dissolution of the present invention, a material containing the attack metal M' is comprised in at least a part of the cathode. Since the material being comprised in a part of the cathode contains the attack metal M', the material acts as a trapping site (deposition site) actively attaching the attack metal M' (Cu, etc.) ion. Incidentally, it is considered that the higher the content of the attack metal M' in the material, the higher the effect of actively attaching the attack metal M' (Cu, etc.) ions becomes. Therefore, the content of the attack metal M' in the material may be 90% by mass % or more, preferably 95% by mass or more, and more preferably 99% by mass or more. Since the deposited attack metal M' and the attack metal M' contained in the material being comprised in a part of the cathode are the same material, their affinity is high, such that the attack metal M' (Cu, etc.) electroplated at the cathode can be suppressed from peeling off after deposition and from precipitating as metal Cu. In addition, it is possible to reduce a supply source of the attack metal M'(Cu, etc.) into the electrolytic solution.

Accordingly, even if the metal compound MxAy having a large difference $\Delta$ in pKsp against the metal compound M'x'Ay' is present, the attack metal M' cannot freely occur exchange (that is, Artifact) with the metal M on the surface of the metal compound MxAy. In other words, generation of M'x'Ay' is suppressed.

Therefore, for example, by preventing Cu ions from attacking MnS on the surface of the steel sample for surface observation, or by preventing metal Cu and CuS from being incorporated into the quantitative analysis residue which is prepared from inclusions and precipitates during the electrolytic operation for identifying and quantitatively analyzing the inclusions and precipitates, it is possible to observe the inclusions and the precipitates in the steel sample for surface observation as they are in their original form. In addition, the electrolytic residue to be analyzed does not contain metal Cu and CuS or the like derived from Cu ions dissolved from the matrix or the like of the sample, which makes it possible to accurately identify and quantitatively analyze only elements originally attributed to the inclusions and precipitates contained in the steel sample.

Cu is remarkable as an attack metal M' which is prone to occur Artifact, due to its content and low solubility product Ksp, in other words, high pKsp. Cu easily attacks the surface of MnS or FeS having a pKsp difference $\Delta$ against the Cu compound of about 20, and can occur Artifact. However, Artifact or the attack by attack metal M' is thought to be more likely to occur as the pKsp difference $\Delta$ is larger. The object of the present invention is not limited to the combination of Cu and MnS or FeS. Specifically, the metal M' of the metal compound M'x'Ay' having a large pKsp may be at least one of Hg, Ag, Cu, Pb, Cd, Co, Zn and Ni, and it can become an attack metal M'. It is considered that the attack metal M' is mainly the one which was eluted into the electrolytic solution from the metal M' or a compound thereof contained in the steel material sample. However, the electrolytic solution or the electrolytic device is sometimes reused, and the metal M' or a compound thereof may be present in the reused electrolytic solution or electrolytic device, which may be an attack metal M'. In the electrolytic extraction operation, the metal M' or a compound thereof may be mixed in the electrolytic solution as a contamination substance and may become an attack metal M'.

M' may be at least one of Hg, Ag, Cu, Pb, Cd, Co, Zn and Ni, but is a metal element different from M. A is a single atom or atomic group forming a compound with M or M' and may comprise one or more atoms independently selected from the group consisting of C, N, H, S, O, P and F atoms. The pKsp difference $\Delta$ between sulfides of Hg, Ag, Cu, Pb, Cd, Co, Zn and Ni, and MnS, is 10 or more. In particular, the pKsp difference $\Delta$ between sulfides of Hg, Ag and Cu, and MnS, is 20 or more.

If the pKsp difference $\Delta$ between the metal compound to be extracted MxAy and the attack metal compound M'x'Ay' is about 10, Artifact can occur in several hours. An actual electrolytic extraction analysis is often carried out in the order of several hours. Therefore, combinations in which the pKsp difference $\Delta$ is about 10 may affect analysis. In the present invention, it is defined that the difference $\Delta$ of pKsp is 10 or more, and in that case, it is possible to suppress Artifact which can occur.

The larger the pKsp difference $\Delta$ between the metal compound to be extracted MxAy and the attack metal compound M'x'Ay', the easier or faster the Artifact can occur. In the present invention, a combination of MxAy and M'x'Ay' having a large pKsp difference Δ can preferably be selected, which makes it possible to suppress Artifact that can easily or quickly occur. In this respect, pKsp [M'x'Ay'] of M'x'Ay' is larger than pKsp [MxAy] of metal compound to be extracted MxAy preferably by 11 or more, more preferably by 12 or more, still more preferably by 13 or more, still more preferably by 14 or more, still more preferably by 15 or more, still more preferably by 16 or more, still more preferably by 17 or more, still more preferably by 18 or more, still more preferably by 19 or more, still more preferably by 20 or more, still more preferably by 21 or more, still more preferably by 22 or more, still more preferably by 23 or more, still more preferably by 24 or more, still more preferably by 25 or more, still more preferably by 26 or more, still more preferably by 27 or more, still more preferably by 28 or more, still more preferably by 29 or more, still more preferably by 30 or more, still more preferably by 31 or more, still more preferably by 32 or more, still more preferably by 33 or more, still more preferably by 34 or more, still more preferably by 35 or more, still more preferably by 36 or more, still more preferably by 37 or more, still more preferably by 38 or more, still more preferably by 39 or more, and still more preferably by 40 or more.

Incidentally, the solubility product Ksp is a value in an aqueous solution, but as shown in Table 2, even when a nonaqueous solvent (lower alcohol) is used, if the pKsp ($-\log_{10} Ksp$) difference Δ obtained from Ksp is 10 or more, it has been confirmed that a reaction proceeds. Specifically, the following confirmation test was conducted.

Two kinds of steel materials containing MnS (one having a particle diameter of MnS of 1 μm or more and the other having a particle diameter of 100 to 150 nm) were prepared as samples containing an object to be extracted, and the surfaces thereof were subjected to a mirror polishing finish.

Six types of standard solution for atomic absorption analysis (M'+ solution) with a metal ion concentration of Ag, Cu, Pb, Co, Zn and Ni of 1000 μg/ml were prepared as attack metal M'+ ions, respectively. 0.1 ml of M' solution was mixed with 0.3 ml of methanol which is a nonaqueous solvent.

Mixed solution was applied to the surface of the steel material to check a change of the steel surface.

In the case of applying the mixed solution containing Ag and Cu, the color of the steel material surface was changed to black within 5 minutes from the application. In the case of applying the mixed solution containing Pb, the color of the steel material surface was changed to black in about 10 minutes from the application. In the case of applying the mixed solution containing Co, Zn and Ni, the color of the steel material surface was changed to black in about 20 minutes from the application.

In addition, SEM and EDS observations were conducted on the steel material which had discoloration, and it was confirmed that exchange of Mn and attack metal M' (that is, Artifact) occurred on the surface of MnS particles.

From this fact, it is presumed that in the scope of the present invention, the solubility product Ksp is an index in an aqueous solution, but it can also be applied to a non-aqueous solution, and the solubility product Ksp therein has the same tendency as in the aqueous solution.

It was also confirmed that the larger the pKsp difference Δ, the faster the exchange (Artifact) reaction occurs. On the other hand, it was also confirmed that, even if the pKsp difference Δ was small, the exchange (Artifact) reaction steadily progressed, although the reaction rate was relatively slow. Electrolytic extraction analysis of steel materials is often done in the order of several hours. For example, the time to immerse the sample in the electrolytic solution may be extended by about 1 hour even if it is planned in about 2 hours. Discoloration was observed in about 20 minutes when using Ni-containing solution and MnS in which the pKsp difference Δ was 10. That is, it was confirmed that the exchange (Artifact) reaction could be problematic when the pKsp difference Δ was 10 or more.

In this connection, in addition to the above confirmation test, a mixed solution of attack metal M'+ solution and methanol plus 0.1 ml of triethylenetetramine (TETA) as a complexing agent (a complexing agent additive solution) was prepared and observation was also carried out when it was applied to a mirror finished steel material. When the complexing agent additive solution was added, discoloration of the surface of the steel material was not observed even after several hours, and a good mirror polished state was maintained. Artifact was not confirmed by SEM and EDS observations.

TABLE 2 pKsp Difference Δ, Expected Occurance of Ion Exchange Reaction in Solvent and Actual Measurement Result

| pKsp Diff. Δ | 0 | 2 | 4 | 6 | 8 | 10 | 12 | 14 | 16 | 18 | 20 |
|---|---|---|---|---|---|---|---|---|---|---|---|
| Reaction (Expect.) | x | x | ✓ | ✓ | ✓ | ✓✓ | ✓✓ | ✓✓ | ✓✓ | ✓✓ | ✓✓✓ |
| Reaction (Actual) | | | | | | ✓Ni | ✓Zn | ✓✓Co | ✓✓Pb | | |

| pKsp Diff. Δ | 22 | 24 | 26 | 28 | 30 | 32 | 34 | 36 | 38 |
|---|---|---|---|---|---|---|---|---|---|
| Reaction (Expect.) | ✓✓✓ | ✓✓✓ | ✓✓✓ | ✓✓✓ | ✓✓✓ | ✓✓✓ | ✓✓✓ | ✓✓✓ | ✓✓✓ |
| Reaction (Actual) | | ✓✓✓Cu | | | | | | | ✓✓✓Ag |

Explanatory Notes:
x no reaction,
✓ reaction in a long time.
✓✓ reaction in several minutes.
and ✓✓✓ reaction in second unit.

The material containing the attack metal M', which is comprised in the cathode may be provided such that the material covers the surface of the cathode. Accordingly, the surface of the cathode acts as a trapping site of the attack metal M' ions, and thus the effect of suppressing peeling off and precipitation of the deposited attack metal M' (Cu, etc.) after deposition will be enhanced.

Alternatively, the cathode may be made of a metal of which a metal compound has said small solubility product Ksp (large pKsp). In other words, an entire cathode is made of the attack metal M', which makes the cathode have a higher affinity to the attack metal M' ions. Accordingly, the cathode more effectively acts as a trapping site of the attack metal M' ions, and thus the effect of suppressing peeling off and precipitation of the deposited attack metal M' (Cu, etc.) after deposition will further be enhanced.

The material made of the attack metal M', which is comprised in the cathode may consist of 99.9% by mass or more of Cu and inevitable impurities. As described before, Cu is remarkable as the attack metal M' which is prone to occur Artifact. By making the material made of the attack metal M' consist of 99.9% by mass or more of Cu and inevitable impurities, the effect of suppressing peeling of and precipitation of Cu as the attack metal M' can surely be enhanced.

A crown ether can be used as a chemical agent that forms a complex containing such an attack metal M'. A crown ether is a cyclic polyether (a series of ether units joined together) and can vary in size of the annular hole. Therefore, depending on the attack metal species M', a crown ether having an appropriate hole can be prepared, thereby only the attack metal species M' can be selectively captured.

The agent that forms a complex containing the attack metal M' may contain any one kind or two or more kinds of polyethylene amines, ethylenediamine tetraacetic acid, cyclohexanediamine tetraacetic acid. They act as a chelating agent and capture the attack metal M'. Examples of polyethyleneamines include triethylenetetramine (TETA), penicillamine, pentaethylenehexamine and the like. In particular, a chelating agent such as triethylenetetramine has a high selectivity for Cu ions, Ni ions, etc., and particularly when the attack metal M' is Cu, Ni or the like, a particularly high capturing effect is exerted.

Table 3 shows the stability constant ($Log_{10}$ Kd) of the complex when Cu or Ni as the attack metal M' is captured with various chelating agents. The higher the stability constant is, the more preferable since it is considered that it is difficult to capture and release the attack metal again. In the case of inhibiting the formation of the compound M'x'Ay, particularly CuS, as an agent that forms a complex containing the attack metal M', one having a stability constant of 10 or more, preferably of 12 or more, more preferably of 14 or more, more preferably of 16 or more, still more preferably of 18 or more, and even more preferably of 20 or more, can be selected. Generally, when a compound in which its formation is to be inhibited M'x'Ay' has a solubility product of Ksp [M'x'Ay'], the agent will be selected such that the difference between pKsp [M'x'Ay'] ($=-Log_{10}$ Ksp [M'x'Ay']) and Log Kd, i.e., pKsp [M'x'Ay']–Log Kd is less than 26, preferably less than 24, more preferably less than 22, more preferably less than 20, still more preferably less than 18, more preferably less than 16.

TABLE 3 the stability constant (Kd) (Log value)
of complex with various chelating agents

| Chelating Agent | Stability Constant ($Log K_d$) | |
|---|---|---|
| | Cu | Ni |
| EDTA: Ethylenediaminetetraacetic acid | 18.3 | 18.2 |
| IDA: Iminodiacetic acid | 10.3 | — |
| $NH_3$ | 4.2 | — |
| EDA: Ethylenediamine | 10.7 | 7.5 |
| DETA: Diethylenetriamine | 16.1 | 10.7 |
| TETA: Triethylenetetramine | 20.4 | 14.0 |
| TEPA: Tetraethylenepentamine | 23.1 | 17.6 |
| PEHA: Pentaethylenehexamine | 26.2 | — |

The attack metal M' is captured and a complex of the attack metal M' is formed. The complex of the attack metal M' is kept dissolved in the above-mentioned solvent. Therefore, even if the metal compound MxAy having a large pKsp difference Δ is present, the attack metal M' cannot freely exchange with the metal M (that is, Artifact) on the surface of the metal compound MxAy. In other words, formation of M'x'Ay' is suppressed.

The chemical agent that forms a complex or the electrolytic solution containing the agent may be agitated in the electrolytic cell. This makes it easier for an unreacted agent to come into contact with the attack metal M', and the attack metal M' is likely to be captured. Means of stirring is not particularly limited, but bubbling by a bubble generator, vortex flow by a magnetic stirrer, or the like may be used. Alternatively, droplets of unreacted agent may be added dropwise in the vicinity of the attack metal M'. The lower limit may be 100 mL/min, preferably 200 mL/min for bubbling and 100 rpm, preferably 200 rpm for a stirrer, so that the unreacted agent can easily contact the attack metal M'. If the bubbling amount or the stirrer rotation speed is too high, problems such as delamination of the surface of the object to be electrolyzed may occur. Therefore, for bubbling, the upper limit may be 600 mL/min, preferably 500 mL/min, and for a stirrer, the upper limit may be 600 rpm, preferably 500 rpm.

Incidentally, in the general electrolytic operation, when stirring the electrolytic solution, stirring operation is performed so that the flow of the electrolytic solution generated by stirring does not come into contact with the electrolytic object. This is based on the idea that the flow of the electrolytic solution generated by stirring does not affect the electrolytic object. In the present invention, from the viewpoint that the chemical agent that forms a complex tends to come into contact with the attack metal M' or a generation source thereof, the agent may be stirred or supplied so that the flow of the electrolytic solution generated by stirring or the like comes into contact with the electrolytic object.

Further, examples of a gas for bubbling include an inert gas such as nitrogen gas, helium, argon and the like. An active gas such as oxygen or hydrogen may affect the concentration of dissolved oxygen in the electrolytic solution, which is not preferable because it may affect the electrolytic object.

According to the present invention, there is also provided a method for extracting metallic compound particles in a metallic material using the same action as the above-mentioned apparatus for electrolytic etching and dissolution. The method relates to a method for extracting metal compound particles in a metal material by electrolytically etching the metal material by providing an anode and a cathode and electrifying between the anode and the cathode. According to this method, in the extracted metal fine particles, the fine particles which are actually MnS and FeS are not erroneously recognized as CuS, and thus it is possible to know the true feature (size, component) of the metal sulfide. Furthermore, the content of the metal sulfide in the steel sample can be accurately comprehended. In addition, according to this method, it becomes possible to observe the extract (for example, inclusions or precipitates exposed on the surface of the steel sample by electrolytic operation) as the components and form originally present in the steel sample. In addition, when quantitatively analyzing inclusions or precipitate components from the analysis of the extract (for example, electrolytic residue), quantitative analysis can be performed correctly without being influenced by Cu or the like incorporated from the electrolytic solution. Therefore, it greatly contributes to the enhancement of the structure observation of the steel sample and the accuracy of identification and quantitative analysis of the inclusions or precipitates in the steel sample.

It has been reported that Mn in the precipitate MnS can be readily exchanged by Se, and MnSe can be precipitated in the steel material, because it is said that MnS and MnSe have the same NaCl type structure and their lattice constants are extremely similar. From the periodic table of elements, it is expected that Te, which is the same group as S or Se, and Sb, which belongs to the adjacent group, easily exchange S of MnS and precipitates as MnTe or MnSb. If MnS is easily exchanged to form MnSe, MnTe and/or MnSb, accurate quantitative analysis of MnS is considered to be useful for improving the accuracy of quantitative analysis of MnSe, MnTe and MnSb.

In addition, MnSe formed by exchange of MnS etc. can further cause an exchange (Artifact) reaction with another selenide. Table 4 shows the pKsp ($=-\log_{10}$ Ksp) difference $\Delta$ among selenides in an aqueous solution at 25° C. In the table, the double line frame (or the dark gray frame) represents a combination of selenides in which the pKsp difference $\Delta$ is 22 or more, and it is expected that the exchange reaction easily proceeds or in unit of seconds with these combinations. Expressed simply as a symbol, the expecting degree (prediction) of the exchange reaction is expressed as √√√. The thick line frame (or light gray frame) represents a combination of selenides in which the pKsp difference $\Delta$ is 10 or more and less than 22, and the exchange reaction is expected to proceed, but it may take from several minutes to several hours. Expressed simply by a symbol, the expecting degree (prediction) of the exchange reaction is expressed as √√ to √. The thin line frame (or the white frame) represents a combination of selenides having the pKsp difference $\Delta$ less than 10, and it is expected that the exchange reaction hardly progresses with these combinations. Expressed simply as a symbol, the expecting degree (prediction) of the exchange reaction is expressed as √ to x.

According to the present invention, it is also possible to prevent Artifact for selenides.

EXAMPLES

Hereinafter, the present invention will be described by means of working examples. However, the present invention should not be construed as being limited to the following examples.

Quantitative analysis of the inclusions or precipitates in steel samples was carried out by electrolytic dissolution using the apparatus for electrolytic etching and dissolution according to the present invention. As a control example, a comparative example electrolyzed using a conventional electrolytic solution was prepared.

In this example, a steel material containing 0.4% by mass of Cu was solutionized by heat treatment at 1350° C. for 30 min and then rapidly cooled in water, and the resulting material was used as a steel sample.

The following two kinds of electrolytic solutions were prepared.

(1) 4% MS: a solution comprising 4% by mass of methyl salicylate+1% by mass of salicylic acid+1% by mass of tetramethylammonium chloride (TMAC) which is conventionally known and can recover sulfide type inclusions as a residue.

(2) 4% MS+5% TETA: 4% MS described in (1) to which 5% by volume of triethylenetetramine (TETA) capable of forming a complex with Cu ion is added.

It is noted that methanol was used as a solvent in both (1) and (2).

For each electrolytic solution, in the case where a cathode electrode is made of Pt plate, and in the case where a cathode electrode is a Cu plate attached to Pt plate, about 1 g of the sample was electrolyzed, and the contents of Mn and Cu contained in the obtained electrolytic residue were quantified by wet chemical analysis, and their contents contained in the 1 g steel sample was calculated. Incidentally, a method for attaching Cu plate to Pt plate was as follows. As Cu plate for attachment, Cu plate having about the same size as Pt plate was prepared. Both the plates were superimposed and are drilled at the edge portions. Pt wires are pass through the holes to fix (tie) these plates to each other.

Figure 2:
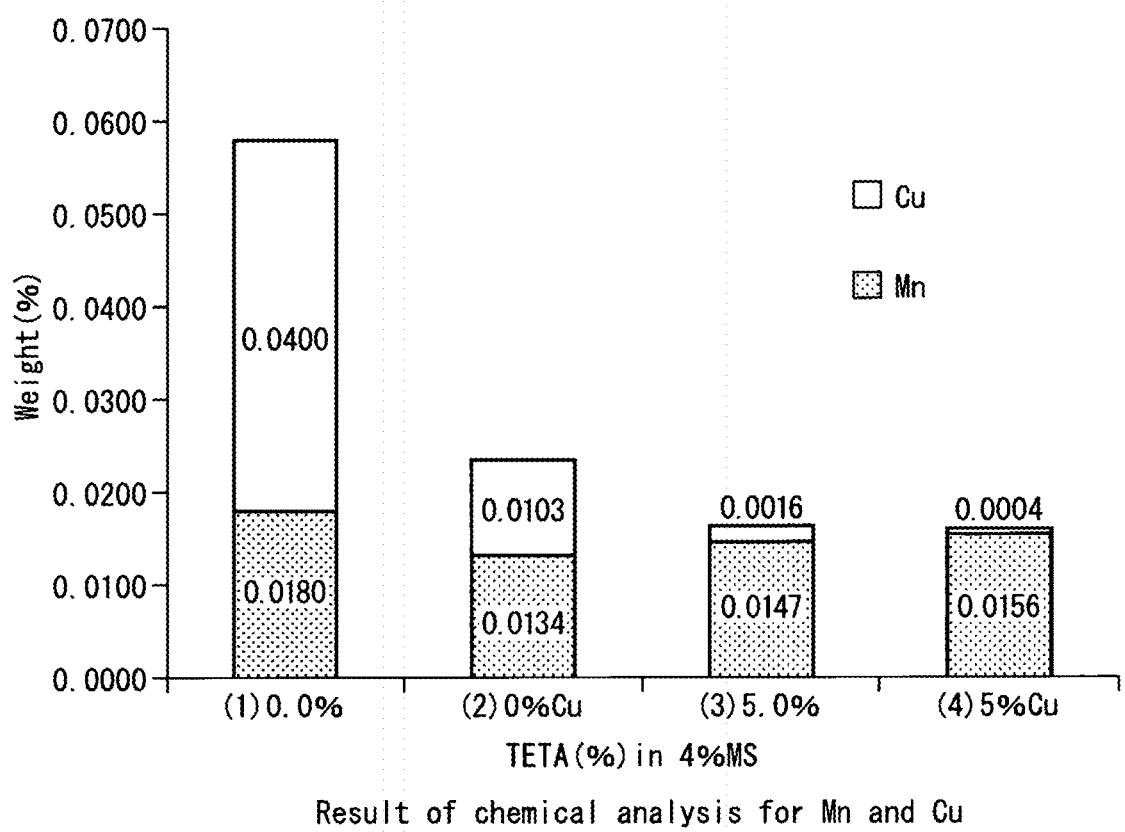
FIG. 2 is a graph showing an analysis result of an electrolytic residue of a steel sample.

The results are shown in FIG. 2.

In the figure, the four band graphs show Mn and Cu detected from the electrolytic residue in % units, respectively. From the left side, (1) the case where the sample was electrolyzed by using Pt plate as a cathode in a generic electrolytic solution (4% MS), (2) the case where the sample was electrolyzed by using the cathode attached by Cu plate in a generic electrolytic solution (4% MS), and (3) the case where the sample was electrolyzed by using Pt plate as a cathode and an electrolytic solution (4% MS+5% TETA) where 5% by volume of TETA was added to the general electrolytic solution, and (4) the case where the sample was electrolyzed by using the cathode attached by Cu plate and an electrolytic solution (4% MS+5% TETA) where 5% by volume of TETA was added to the general electrolytic solution.

When the steel samples adopted in the examples were mirror polished and the distribution of its component elements was analyzed by EDS or the like, it was confirmed that the Cu contained in the sample was mostly solid-solved in the sample matrix portion, and was not present in sulfide form such as CuS and $Cu_2S$.

Nonetheless, in the electrolytic dissolution using the conventional Pt electrode as a cathode, and the electrolytic solution (4% MS) shown in (1) of FIG. 2, Cu concentration (0.04%=400 ppm) which is higher than Mn concentration (0.018% by mass) was measured from the electrolytic residue whose main component is sulfide in the steel sample. The reason for this is considered as follows. Attack metal (Cu) dissolved out from the steel sample is deposited at the Pt cathode. However, after deposition, it easily peels off and precipitates as metal Cu in the residue, or precipitates in the electrolytic solution to form a supply source of the attack metal (Cu). With the attack metal (Cu) supplied from this supply source, the surface of the metal compound (MnS) was exchanged by metal (Cu) (i.e., Artifact) to produce CuS.

The graph shown in (2) shows the case where a Cu plate was attached to the cathode made of Pt and electrolytic dissolution was performed with an electrolytic solution (4% MS). Cu component in the electrolytic residue was reduced to 0.0103% by mass (103 ppm). This is because the Cu plate fixed to the Pt cathode acted as a trapping site (deposition site) of attack metal (Cu) ions, suppressed peeling/precipitation after the deposition of attack metal (Cu) electrodeposited at the cathode. As a result, it is considered that the metal Cu precipitating in the residue, or the supply source of the attack metal (Cu) into the electrolytic solution were reduced.

In addition, the graph shown in (3) shows the concentrations of Mn and Cu measured from the electrolytic residue when electrolyzing with the electrolytic solution (4% MS+5% TETA) added with 5 vol % of triethylenetetramine using the Pt electrode as the cathode.

In this case, the content of Cu in the electrolytic residue was decreased to 0.0016% by mass (16 ppm). This is because it is thought that triethylenetetramine (TETA) forms a complex with the Cu ion, which suppresses that the attack metal (Cu) is exchanged with the metal (Mn) on the surface of the metal compound (MnS) (i.e., Artifact).

Furthermore, (4) shows measured values when the electrolytic solution containing TETA (4% MS+5% TETA) and attachment of the Cu plate to the cathode made of Pt were used in combination.

It was found that the Cu concentration measured from the electrolytic residue was decreases to 0.0004% by mass (4 ppm), and it was possible to reduce the Cu concentration to 5 ppm or less, which is the measurement limit in an ordinary analysis.

That is, by electrolyzing a metal sample using the apparatus for electrolytic etching and dissolution that comprises a material consisting of an attack metal as at least a part of the cathode, the chemical analysis accuracy of the residue is improved, and inclusions and precipitates present in the sample can be accurately identified and quantified.

INDUSTRIAL APPLICABILITY

By electrolyzing a metal sample using the apparatus for electrolytic etching and dissolution that comprises a material consisting of an attack metal as at least a part of the cathode, it becomes possible to observe inclusions and precipitates in the sample in the form originally present in the sample. Further, in chemical analysis of the inclusions and precipitates, contamination due to incorporation of Cu etc. can be eliminated, and the accuracy of chemical analysis can be improved.

REFERENCE SIGNS LIST 4 metal sample
5 inclusions and precipitate grains
6 electrode (cathode side)
7 reference electrode
8 power supply (potentiostat)
9 electrolytic solution
10 electrolytic cell
11 electrolytic residue

The invention claimed is:

1. An apparatus for electrolytic etching and dissolution, the apparatus comprising:
an electrolytic cell comprising an anode, a cathode and an electrolytic solution comprising a chemical agent and a nonaqueous solvent;
wherein the chemical agent comprises at least one of a polyethylene amine, ethylenediamine tetraacetic acid and cyclohexanediamine tetraacetic acid, and the non-aqueous solvent comprises at least one of methanol, ethanol and isopropyl alcohol;
wherein at least a part of the cathode comprises a metal element M', the anode comprises a metal material including a different metal element M;
wherein the metal element M' whose A is defined by the following formula is 10 or more:

$$\Delta = pKsp[M'x'Ay'] - pKsp[MxAy] =$$
$$(-\log_{10}Ksp[M'x'Ay']) - (-\log_{10}Ksp[MxAy])$$

wherein a solubility product of metal compound M'x'Ay' is defined as Ksp[M'x'Ay'], and a solubility product of a metal compound to be extracted from the anode is MxAy, defined as Ksp[MxAy], the solubility product Ksp is a value in an aqueous solution at 25° C.; and
A consists of one or more of C, N, H, S, O, P, Se, Te and F for forming a compound with M or M', and x, x', y and y' represent a composition ratio of the compound determined according to the valences of M, M' and A; and
electrolytically etching the anode to extract the metal compound MxAy by electrifying between the anode and the cathode.

2. The apparatus of claim 1, wherein the metal element M' is at least one of Hg, Ag, Cu, Pb, Cd, Co, Zn and Ni.

3. The apparatus of claim 1, wherein the metal compound MxAy is at least one of FeS and MnS.

4. The apparatus of claim 3, wherein the metal element M' is at least one of Hg, Ag, Cu, Pb, Cd, Co, Zn and Ni.

5. The apparatus of claim 1, wherein the metal element M' is provided to cover a surface of the cathode.

6. The apparatus of claim 1, wherein the cathode consists of the metal element M'.

7. The apparatus of claim 6, wherein the metal element M' consists of 99.9% or more of copper by mass.

8. The apparatus of claim 1, wherein the polyethylene amine of the chemical agent comprises triethylenetetramine.

9. The apparatus of claim 1, wherein the apparatus further comprises a stirring means for the electrolytic solution.

10. The apparatus of claim 9, wherein the stirring means is a gas bubble generator.

11. A method for extracting metal compound particles in a metal material, the method comprising:
providing an electrolytic cell comprising an anode, a cathode and an electrolytic solution comprising a chemical agent and a nonaqueous solvent;
wherein the chemical agent comprises at least one of a polyethylene amine, ethylenediamine tetraacetic add and cyclohexanediamine tetraacetic add, and the non-aqueous solvent comprises at least one of methanol, ethanol and isopropyl alcohol;
wherein at least a part of the cathode comprises a metal dement M', the anode comprises the metal material including a different metal demerit M;
wherein the metal dement M whose A is defined by the following formula is 10 or more:

$$\Delta = pKsp[M'x'Ay'] - pKsp[MxAy] =$$
$$(-\log 10 Ksp[M'x'Ay']) - (-\log 10 Ksp[MxAy])$$

wherein a solubility product of metal compound M'x'Ay' is defined as Ksp[M'x'Ay'], and a solubility product of a metal compound to be extracted from the anode is MxAy, defined as Ksp[MxAy], the solubility product Ksp is a value in an aqueous solution at 25° C.; and A consists of one or more of C, N, H, S, O, P, Se, Te and F for forming a compound with M or M', and x, x', y and y represent a composition ratio of the compound determined according to the valences of M, M' and A; and electrolytically etching the anode to extract the metal compound MxAy by electrifying between the anode and the cathode.

12. The method of claim 11, wherein the metal element M' is at least one of Hg, Ag, Cu, Pb, Cd, Co, Zn and Ni.

13. The method of claim 11, wherein the metal compound MxAy is at least one of FeS and MnS.

14. The method of claim 13, wherein the metal element M' is at least one of Hg, Ag, Cu, Pb, Cd, Co, Zn and Ni.

15. The method of claim 11, wherein the metal element M' is provided to cover a surface of the cathode.

16. The method of claim 11, wherein the cathode consists of the metal element M'.

17. The method of claim 16, wherein the metal element M' consists of 99.9% or more of copper by mass.

18. The method of claim 11, wherein the polyethylene amine of the chemical agent comprises triethylenetetramine.

19. The method of claim 11, wherein the electrolytic solution is stirred during the electrolytic etching process.

20. The method of claim 19, wherein the stirring is performed by a magnetic stirrer or a gas bubble generator.

* * * * *